United States Patent
Seegmiller

(10) Patent No.: US 6,221,861 B1
(45) Date of Patent: Apr. 24, 2001

(54) REDUCING PYROPHOSPHATE DEPOSITION WITH CALCIUM ANTAGONISTS

(75) Inventor: J. Edwin Seegmiller, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/350,694

(22) Filed: Jul. 9, 1999

Related U.S. Application Data

(60) Provisional application No. 60/092,401, filed on Jul. 10, 1998.

(51) Int. Cl.[7] .................. A61K 31/55; A61K 31/495; A61K 31/44; A61K 31/275
(52) U.S. Cl. ................ 514/220; 514/255.01; 514/357; 514/523; 514/825
(58) Field of Search ........................... 514/220, 523, 514/357, 255.01, 825

(56) References Cited

FOREIGN PATENT DOCUMENTS

92/16226 * 10/1992 (WO) ................................ 514/220

OTHER PUBLICATIONS

Ali, S. Yousuf, "Calcification of Cartilage," *Cartilage*, Hall, Brian K. (ed.) 1983, 1:343–78. (Exhibit 1).

Anderson, H. Clarke, "Mechanisms of Pathologic Calification," *Rheumatic Disease Clinics of North America*, Aug. 1988, 14(2):303–19. (Exhibit 2).

Derfus, Beth A. et al., "Articular Cartilage Vesicles Generate Calcium Pyrophosphate Dihydrate/–Like Crystals in Vitro," *Arthritis and Rheumatism*, Feb. 1992, 35(2):231–40. (Exhibit 3).

Jones, Adrian C. et al, "Diseases Associated With Calcium Pyrophosphate Deposition Disease," *Seminars in Arthritis and Rheumatism*, Dec. 1992, 22(3):188–202. (Exhibit 4).

Lust, G. et al., "Increased Pyrophosphate in Fibroblasts and Lymphoblasts from Patients with Hereditary Diffuse Articular Chondrocalcinosis," *Science*, Nov. 13, 1981, 214:809–10. (Exhibit 5).

Lust, G. et al., "Inorganic Pyrophosphate and Proteoglycan Metabolism in Cultured Human Articular Chrondrocytes and Fibroblasts," *Arthritis and Rheumatism*, May–Jun. 1976, 19(3):479–87. (Exhibit 6).

Rachow, John W. and Ryan M. Lawrence, "Inorganic Pyrophosphate Metabolism in Arthritis," *Rheumatic Disease Clinics of North America*, Aug. 1988, 14(2):289–302. (Exhibit 7).

Rasmussen, Howard, "Hypophosphatasia," *The Metabolic Basis of Inherited Disease*, Stanbury, John B. et al. (eds.) 1983, pp1497–1507. (Exhibit 8).

Rosen, Fred et al., "Differential Effects of Aging on Human Chondrocyte Responses to Transforming Growth Factor β Increased Pyrophosphate Production and Decreased Cell Proliferation," *Arthritis and Rheumatism*, Jul. 1997, 40(7):1275–81. (Exhibit 9).

Rosenthal, Ann K. et al., "A Comparison of the Effect of Transforming Growth Factor β1 on Pyrophosphate Elaboration From Various Articular Tissues," *Arthritis and Rheumatism*, Apr. 1993, 36(4):539–42. (Exhibit 10).

Russell, R.G.G. et al., "The Influence of Pyrophosphate, Condensed Phosphates, Phosphonates and other Phosphate Compounds on the Dissolution of Hydroxyapatite in vitro and on Bone Resorption Induced by Parathyroid Hormone in Tissue Culture and in Thyroparathyroid Hormone in Tissue Culture and in Thyroparathyroidectomised Rats," *Calcified Tissue Research*, 1970–71, 6:183–96. (Exhibit 11).

Ryan, Lawrence M., and Daniel J. McCarthy "Calcium Pyrophosphate Crystal Deposition Disease; Psuedogout; Articular Chondrocalcinosis," *Arthritis and Allied Conditions*, McCarty, Daniel J and William J. Koopman (eds.) 1993, 2(12th Edition):1835–55. (Exhibit 12).

Ryan, Lawrence M. et al., "Pyrophosphohydrolase Activity and Inorganic Pyrophosphate Content of Cultured Human Skin Fibroblasts Elevated Levels in Some Patients With Calcium Pyrophosphate Dihydrate Deposition Disease," *The Journal of Clinical Investigation*, May 1986, 77(5):1689–93 (Exhibit 13).

Schroeder Jr., Harry W., "Immunoglobulins and Their Genes," *Arthritis and Allied Conditions*, McCarty, Daniel J and William J. Koopman (eds.) 1993, 2(12th Edition):335–45. (Exhibit 14).

Siegel, Scott A. et al., "The Role of Nucleoside Triphosphate Pyrophosphohydrolase in in Vitro Nucleoside Triphosphate–dependent Matrix Vesicle Calcification," *The Journal of Biological Chemistry*, Jul. 25, 1983, 258(14):8601–7, (Exhibit 15).

Tenenbaum, Jerry et al., "Comparison of Phosphohydrolase Activites From Articular Cartilage in Calcium Pyrophosphate Deposition Disease and Primary Osteoarthritis," *Arthritis and Rheumatism*, Mar. 1981, 24(3):492–500. (Exhibit 16).

Terkeltaub, Robert A., "Pathogenesis and Treatment of Crystal–Induced Inflammation," *Arthritis and Allied Conditions*, McCarty, Daniel J and William J. Koopman (eds.) 1993, 2(12th Edition):1819–33. (Exhibit 17).

* cited by examiner

Primary Examiner—Frederick Krass
(74) Attorney, Agent, or Firm—Mandel & Adriano

(57) ABSTRACT

This invention provides a method of treating an animal with pyrophosphate gout or osteoarthritis comprising administering an effective amount of a calcium antagonist, thereby reducing calcium pyrophosphate crystal deposition in the animal.

10 Claims, No Drawings

REDUCING PYROPHOSPHATE DEPOSITION WITH CALCIUM ANTAGONISTS

This subject application claims the priority of provisional application, U.S. Ser. No. 60/092,401, filed Jul. 10, 1998.

This invention was made with U.S. Government support under Grant No. AG07996, awarded by the National Institutes of Health. The Government has certain rights in this invention.

FIELD OF THE INVENTION

The invention is directed to the use of an existing class of calcium blocking drugs, or calcium antagonists for the correction of an underlying metabolic abnormality responsible for calcium pyrophosphate crystal formation and the resulting development of one of the most recently recognized forms of crystal-induced arthritis from deposition of these crystals in the cartilage of major joints.

BACKGROUND OF THE INVENTION

The first two decades of the past half-century marked the first successful treatment in a preventive mode of the most anciently recognized form of crystal-induced arthritis— gouty arthritis, by simply reducing the supersaturated concentrations of serum urate to the normal range by use of new drugs that became available. (Seegmiller, J E., "Conquest of Gouty Arthritis" in *Landmark Advances in Rheumatology*, ed. McCarty, D J (Amer. Rheum. Assn., Atlanta, Ga.) pp. 89–101 (1985)). It may well serve as a model for similar success with the above new and as yet unpublished finding. An important difference is that the elevated pyrophosphate was first found inside, instead of outside, the cells (Lust, G., et al. *Arthritis Rheum* (1976) 19:479–487). Inorganic pyrophosphate (PPi) serves a number of different biological functions. In bone and growth plate cartilage, extracellular inorganic PPi provides a critical source of phosphate (Pi) for the physiologic deposition of calcium phosphate crystals during bone mineralization (Ali, Y., "Calcification of Cartilage" in *Cartilage: Structure, Function, Biochemistry*, ed. Hall, BK (Academic, New York), pp. 343–378 (1983); Oyajobi, B O, et al., *J Bone Miner Res* (:1259–1266 (1944); Anderson, H C, *Rhem Dis Clin North Am* 14:303–319 (1988), and Rosen et al., Arthritis & Rheumatism, 40:7 (July 1997)).

Although PPi is required for the induction of calcification (Russell, R G, et al., *Calcif Tissue Res.* (1970) 6:183–196; Siegel, S A et al., (1983) *J Biol Chem* 258:8601–8607), an excess of free PPi in relation to Pi suppresses mineralization by inhibiting hydroxyapatite crystal nucleation from amorphous calcium phosphate (Ali, Y., "Calcification of Cartilage" in *Cartilage: Structure, Function, Biochemistry*, ed. Hall, BK (Academic, New York), pp. 343–378 (1983); Oyajobi, B O, et al., *J Bone Miner Res* (:1259–1266 (1944); Anderson, H C, *Rhem Dis Clin North Am* 14:303–319 (1988), and Rosen et al., Arthritis & Rheumatism, 40:7 (July 1997)). Chondrocytes in articular cartilage have the unique ability to constitutively elaborate extracellular PPi in large amounts (Rosenthal, A K et al. (1993) *Arthritis Rheum.* 36:539–542; Derfus, B A et al., *Arthritis Rheum* 35:231–240 (1992)), which helps to suppress mineralization of the avascular cartilage matrix (Poole, A R (1992) in *Arthritis and Allied Conditions*, eds., McCarty, D J and Koopman, W J (Lea & Febiger, Philadelphia), pp. 335–345).

PPi elaboration is governed by the balance between PPi formation and degradation (Rachow, J W and Ryan, L M (1988) *Rheum Dis Clin North Am* 14:289–302). PPi generation is a byproduct of many synthetic reactions in the cell (Rachow, J W and Ryan, L M (1988) *Rheum Dis Clin North Am* 14:289–302) and is a direct product of enzymes that have nucleoside triphosphate pyrophosphohydrolase (NTPPPH) activity. PPi degradation is affected by several inorganic pyrophosphatases, including alkaline phosphatase. (Rachow, J W and Ryan, L M (1988) *Rheum Dis Clin North Am* 14:289–302, Rasmussen, H. (1983) in *The Metabolic Basis of Inherited Disease*, eds. Stanbury, H., et al., (McGraw-Hill, New York), pp. 1497–1507).

Regulation of NTPPPH activity, and of other factors that modulate elaboration of extracellular PPi in cartilage and bone, appears critical not only to physiologic mineralization, but also to the development of certain disorders of pathologic mineralization (Anderson, H C, *Rhem Dis Clin North Am* 14:303–319 (1988). One example is a prevalent disease of the elderly known as idiopathic chondrocalcinosis. In this disease, the deposition of calcium pyrophosphate dihydrate (CPPD) crystals in articular cartilage is strongly linked to substantial increases in NTPPPH activity and PPi concentration (Tenenbaum, J. et al., (1981) *Arthritis Rheum* 24:492–500; Ryan, L M and McCarty, D J (1992) in *Arthritis and Allied Conditions*, eds., McCarty, D J and Koopman, W J (Lea & Febiger, Philadelphia), pp. 1835–1856; Jones, A C, et al., (1992) *Semin Arthritis Rheum* 22:188–202).

In addition, a 2–3-fold increase in intracellular PPi has been found in cartilage cells, fibroblasts, and lymphoblasts cultured from chondrocalcinosis patients (Lust, G. et al., (1976) *Arthritis Rheum* 19:479–487; Lust, G., et al., (1981) *Science* 214:809–810; Ryan, L M, et al. (1986) *J Clin Invest* 77:1689–1693). The capacity of CPPD crystals to activate an inflammatory response can promote acute and chronic inflammatory synovitis and cartilage degeneration (Ryan, L M and McCarty, D J (1992) in *Arthritis and Allied Conditions*, eds., McCarty, D J and Koopman, W J (Lea & Febiger, Philadelphia), pp. 1835–1856; Terkeltaub, R. (1992) in *Arthritis and Allied Conditions*, eds. McCarty, D J and Koopman, W J (Lea & Febiger, Philadelphia), pp. 1819–1833). Moreover, the presence of CPPD crystal deposition commonly complicates prior articular injury and is an adverse prognostic factor in osteoarthritis (Ryan, L M and McCarty, D J (1992) in *Arthritis and Allied Conditions*, eds., McCarty, D J and Koopman, W J (Lea & Febiger, Philadelphia), pp. 1835–1856; Sokoloff, L. & Varma, A A (1988) *Arthritis Rheum* 31:750–756).

"Pseudogout" was the term first used to describe the clinical syndrome of acute gout-like arthritis associated with the presence of crystals of calcium pyrophosphate dihydrate in synovial fluid (McCarty, D J et al., I. Clinical aspects. *Ann Intern Med* 56:711 (1962). Also, see Seegmiller, J E, "Gout and Pyrophosphate Gout (Chondrocalcinosis,") in *Principles of Geriatric Medicine and Gerontology*, Third Edition, 1994, Hazzard, W., et al., eds., McGraw-Hill, Inc., pp. 987–994). Subsequent studies showed this gout-like presentation to be just one aspect of the far larger range of clinical presentations of patients showing radiologic evidence of a characteristic pattern of calcification within the joints, which is called "chondrocalcinosis" (Zitnan, D., and Sitaj, D., *Cesk Radiol* 14:27 (1960)) and more precisely designated as "calcium pyrophosphate dihydrate crystal deposition disease" (CPDD) (Ryan, L M, and McCarty, D J, "Calcium Pyrophosphate Crystal Deposition Disease: Pseudogout: Articular Chondrocalcinosis," in McCarty, D J (ed): *Arthritis and Allied Conditions: A Textbook of Rheumatology*, 10th ed., Philadelphia, Lea & Febiger, 1985, p. 1515). Since these multiple names for the same basic pathological process are confusing to both students and professionals, a subcommittee of the American College of Rheumatology has recommended the name "pyrophosphate gout" as being a more specific and simple designation for naming this disorder in a whole family of pathological states that would include apatite gout, cholesterol gout, and oxalate gout, with the prototype, urate gout, being referred to simply as "gout." (Simkin, P A, *JAMA* 260:1285 (1988)).

Pyrophosphate gout shows similarities to gouty arthritis in that it is a crystal-induced arthritis with intermittent acute attacks associated with appearance of crystals within phagocytes in the joint fluid and a consequent acute inflammatory reaction (Ryan, L M, and McCarty, D J, "Calcium Pyrophosphate Crystal Deposition Disease: Pseudogout: Articular Chondrocalcinosis," in McCarty, D J (ed): *Arthritis and Allied Conditions: A Textbook of Rheumatology*, 10th ed., Philadelphia, Lea & Febiger, 1985, p. 1515; McCarty, D J, et al, (1962), Ann Intern Med 56:711). The overall incidence of pyrophosphate gout increases markedly in later years of life. It is seldom seen in patients below age 50 except in familial forms of the disease. However, X-ray evidence of the disease has been found in some 44 percent of patients over age 84 and in 50 percent of patients in a nursing home over age 90 (Wilkins, E et al. *Ann Rheum Dis* (1983) 42:280–284).

Instead of needle-shaped crystals of monosodium urate monohydrate deposited in and about the joint as seen in gouty arthritis, the deposits of crystals in pyrophosphate gout consist of rhombic or broad-shaped crystals of calcium pyrophosphate dihydrate that are typically found as a punctate or lamellar layer in the midzone of the cartilage. This is most often seen on x-ray films of the knee in meniscal fibrocartilage, as well as in the articular cartilage of the knee, in the articular disk of the distal radioulnar joint of the wrists, and, less frequently, in and about other major joints (Resnick, D., *JAMA* (1979) 242:2440).

Several large pedigrees of hereditary pyrophosphate gout have been reported, most of which show evidence of a dominant pattern of inheritance (Seegmiller, J E, in Emery A., Rimoin, D (eds): *The Principles and Practices of Medical Genetics*, 2d ed. New York, Churchill Livingstone (1990), p. 1697; Van der Korst, J K and Gerard, *J. Arthritis Rheum* (1976) 19:405; Reginato, A J, *Arthritis Rheum* (1976) 19:395; McKusick, V.: *Mendelian Inheritance in Man*, 7th ed. (1986) The Johns Hopkins University Press). The close association of osteoarthritis and pyrophosphate gout (Wilkins, E et al. *Ann Rheum Dis* (1983) 42:280) has been recently confirmed by autopsy studies showing a frequency of concurrence of these diseases sixfold greater than would be expected from the chance association represented by the respective frequencies of both individual diseases in the population (Sokoloff, L, and Varma, A A, *Arthritis Rheum* (1988) 31:750). The discovery of modest elevations of pyrophosphate levels in synovial fluid of patients with more severe osteoarthritis suggests a possible metabolic link between the two diseases (Howell, D S, et al. *Arthritis Rheum* (1976) 19:488–494). Further evidence of such a link was found in chondrocytes cultured from normal, osteoarthritic and pyrophosphate gout (chondrocalcinosis) patients. The intracellular PPi was 2-fold over normal in the pyrophosphate gout patients and the osteoarthritis patients showed values intermediate between the two (Lust, G. et al. *Arthritis Rheum* (1976) 19:479–487). In unpublished work from the inventor's laboratory mononuclear cells isolated from peripheral blood also showed a significantly higher than normal concentration of intracellular PPi presented in Table 3 of this document.

Until the present invention, no rational approach was known for correction of the underlying metabolic abnormality responsible for calcium pyrophosphate crystal formation and the resulting development of disease (Seegmiller, J E, "Gout and Pyrophosphate Gout (Chondrocalcinosis)," in *Principles of Geriatric Medicine and Gerontology*, Third Edition, 1994, Hazzard, W., et al., eds., McGraw-Hill, Inc., pp. 987–994).

This invention provides an unexpected use for an existing class of calcium blocking drugs, or calcium antagonists. During early clinical application of a new assay for pyrophosphate developed in the inventor's laboratory (Barshop, B A et al. *Analyt Biochem* (1991) 197:266–272), the inventors unexpectedly found that the calcium channel antagonists, nifedipine or diltiazem, widely used for management of hypertension, also lowers the intracellular concentration of pyrophosphate (PPi), and therefore should be useful for treatment of illnesses caused by the near 2-fold increase above normal of the intracellular PPi first found earlier by the inventor's laboratory in chondrocytes cultures from a patient with pyrophosphate gout (then called chondrocalcinosis) while the corresponding fibroblasts cultured from the same patient showed PPi values some 2.6 fold greater than the normals with less marked elevations found in patients with osteoarthritis (Lust, G. et al. *Arthritis Rheum* (1976) 19:479–487) calcium pyrophosphate crystal deposition, of pyrophosphate gout or less marked elevations of intracellular PPi we had found in patients with osteoarthritis.

Calcium antagonists are heterogeneous and fall into 3 major classes: the phenylalkylamines (verapamil), the dihydropyridines (nifedipine), and the benzothiazepines (diltiazem). Although Palmieri, et al, (Arth. & Rhem. 38:1646–1654 (1995) report dissolution of calcinosis in the cervical spine in a patient by long-term administration of diltiazem, this illness was designated as CREST syndrome, a more indolent and less severe sub-type of progressive systemic sclerosis (scleroderma). With its limited cutaneous involvement, skin thickening and scarring of the skin is most often limited to the face and/or hands. This variant has been designated CREST, an abbreviation for its components (calcinosis, Raynaud's phenomenon, esophageal hypomotility, sclerodactyly, and telangectasia) (Medsger, T A, "Systemic Sclerosis (Scleroderma)" in *Internal Medicine*, ed. Stein, J H (Mosby-Year Book, Inc., Baltimore), pp. 2443–24 (1949)). Since specific autoantibodies are also found in most cases and the calcinosis involves the extracellular deposition of calcium phosphate nodules, CREST syndrome is quite unrelated to pyrophosphate gout in either clinical or biochemical features. Therefore, this invention provides the first rational use of calcium antagonists for rational treatment of illnesses caused by calcium pyrophosphate crystal deposition.

SUMMARY OF THE INVENTION

The present invention provides a rational method for treatment of an animal with pyrophosphate gout comprising administering an effective amount of a calcium antagonist, thereby reducing calcium pyrophosphate crystal deposition in the animal.

The present invention also provides a reasonable approach for the correction of the less marked elevation of intracellular PPi which we have also found in patients with osteoarthritis (see Table 3 enclosed) which should also prevent the 6-fold greater than expected tendency they have for also developing pyrophosphate gout. By analogy with the human, this method of treating an animal with osteoarthritis comprising administering an effective amount of a calcium channel antagonist and thereby reduce, thereby calcium pyrophosphate crystal deposition in the animal.

DETAILED DESCRIPTION OF THE INVENTION

The present invention provides a method of treating an animal with pyrophosphate gout or osteoarthritis comprising administering an effective amount of a calcium antagonist, thereby reducing calcium pyrophosphate crystal deposition in the animal. The animal can be a mammal, which may be an animal typically used for experimentation, such as mice, rats or rabbits. Preferably, the mammal is a human. As used in this application, pyrophosphate gout includes chondrocalcinosis, pseudogout, and any other disease caused by calcium pyrophosphate dihydrate crystal deposition.

The calcium antagonist is a channel blocking drug that falls into one of four classes: (1) the phenylalkylamines, such as verapamil, gallopamil, (2) the dihydropyridines, such as nicardipine, nifedipine, and nimodine (3) the benzothiazepines, such as diltiazem and (4) the diphenylpiperazines. Preferably, the calcium channel blocking drug is diltiazem or nifedipine.

The calcium antagonists described herein may be in a variety of dosage forms which include, but are not limited to, liquid solutions or suspensions, tablets, pills, powders, suppositories, polymeric microcapsules or microvesicles, liposomes, and injectable or infusible solutions. The preferred form depends upon the mode of administration and the therapeutic application.

The most effective mode of administration and dosage regimen for the molecules of the present invention depends upon the severity and course of the disease, the subject's health and response to treatment and the judgment of the treating physician. Accordingly, the dosages of the molecules should be titrated to the individual subject.

Dosages of the calcium antagonists include but are not limited to the following. The dosage for nifedipine can be 30–60 mg daily. For nicardinipine hydrochloride, a recommended dosage can be 60–120 mg daily. For nimodipine, a dosage can be 240 mg daily. For verapamil, a dosage can be 240–360 mg daily. For example, a dosage for diltiazem hydrochloride is 360 mg daily.

The following examples are presented to illustrate the present invention and to assist one of ordinary skill in making and using the same. The examples are not intended in any way to otherwise limit the scope of the invention.

EXAMPLE 1

The two-fold elevation in intracellular PPi our laboratory had found in permanent lymphoblast lines cultured from affected as compared to non-affected members of a family with familial pyrophosphate gout (Lust, G et al. *Arthritis Rheum* (1981) 24:1517–1521) suggested the use of mononuclear cells isolated directly from peripheral blood as a more direct assay.

Mononuclear Cell Isolation: For this purpose 5 ml of freshly drawn heparinized blood was layered on 3.0 ml of Histopaque in a 15 ml polypropylene centrifuge tube and centrifuged at room temperature for 20 minutes at 1,000 g. The mononuclear cell layer was then removed from the tube and transferred into a new 15-ml tube. Volume was brought to a total of 5 ml by addition of Hanks buffered salt solution lacking Mg and Ca (HBSS). This suspension of cells was again layered onto 3.0 ml of Histopaque and again centrifuged as before.

Resuspension of the centrifuged cells in 12-ml HBSS was repeated three times, each followed by 10 min centrifugation at a lower g of 250 g, 50 g, and 50 g to remove contaminating platelets which carry substantial PPi. The importance of these last washings was not realized in our initial study shown in Table 1 and 2 which accounts for the higher general values of PPi recorded there for normal than in subsequent tables.

After decanting the supernatant, the cell pellet was resuspended in 1.0 ml of HBSS for counting in a hemocytometer. After counting, the cell suspension was spun for 10 minutes in a microfuge at 14,000 rpm. After decanting and thoroughly removing the supernatant, 3.0 $\mu$l of 0.1 M sodium periodate (an alkaline phosphatase inhibitor) were added and the cells were lysed by addition of 100 $\mu$l of 1% triton X-100 and vortexing. The lysate is then stored frozen at −20° C. until time of assay.

PPi Assay: The assay of PPi in mononuclear cells in Tables 1 and 2 were done by the luminescent methods (Barshop, B A et al. *Analyt Biochem* (1991) 197:266–272). Subsequent analyses were done with a time-tested radioisotope method which gave essentially the same values after platelet associated PPi contaminations present in Tables 1 & 2 were removed during sample preparation (Cheung, C P and Suhadolnik, R J *Anal Biochem* (1977) 83:61–63) with improvements (McGuire, M B et al. *Biochem Soc Trns* (1980) 8:529–530). Each sample was assayed in duplicate and in the presence and absence of added pyrophosphate as a recovery test.

Discussion

Table 1 shows the first group of normal volunteer in which the measurement of intracellular PPi content of mononuclear cells isolated from peripheral blood was determined. The unexpectedly low values of volunteer J.S. compared to the other two resulted in a closer examination of medications each were taking. J.S. had been recently started on daily nifedipine for a borderline elevation of blood pressure. With his internist's consent the dose was stopped for two weeks prior to the next determination which showed values over 2 fold higher. Upon resuming the nifedipine the PPi values again decreased over the next 5 months to a value ⅓ of that found off the medication. Volunteer N.M. was an adult woman volunteer who had just been scheduled by the same internist to start the same medication for her hypertension. It is not known for certain that she had been taking the full scheduled dose.

Table 2 shows a comparable lowering of mononuclear cells in one of two patients with chondrocalcinosis (pyrophosphate gout) who were started on diltiazem.

Table 3 shows a less markedly elevated intracellular PPi of patients with osteoarthritis.

These drugs and this new analytical procedure hold the potential of providing a preventive approach to treatment of pyrophosphate gout and possibly osteoarthritis in a preventive mode quite comparable to that now achieved for gouty arthritis.

TABLE 1

EVIDENCE THAT NIFEDIPINE CAN LOWER THE INTRACELLULAR PPi LEVELS in vivo IN HUMAN PERIPHERAL BLOOD LYMPHOCYTES

| SUBJECT | COLLECTION DATE | NIFEDIPINE (mg/day) | PPi (pmole/10 cells) |
|---|---|---|---|
| B.R. | | 0 | 272 ± 86 |
| F.R. | | 0 | 269 |
| J.S. | 11/13/90 | 60 | 138 ± 34 |
| | 01/04/91 | 0 | 309 ± 66 |
| | 01/15/91 | 60 | 120 ± 5 |
| | 03/07/91 | 60 | 101 ± 4 |
| N.M | 03/01/91 | 0 | 188 ± 26 |
| | 03/07/91 | 90 | 126 ± 18 |

Date are expressed as Mean values (r S.D.) of triplicate determinations.

TABLE 2

EVIDENCE THAT DILTIAZEM CAN LOWER THE INTRACELLULAR PPi LEVELS in vivo IN PERIPHERAL BLOOD LYMPHOCYTES OBTAINED FROM TWO PATIENTS AFFECTED BY ATRICULAR CHONDROCALCINOSIS

| Subject | Collection Date | Diltiazem (mg/day) | PPi (pmole/$10^6$ cells) |
|---|---|---|---|
| W.P. (chondrocalcinosis) | 01/03/91 | 0 | 342 |
| | 03/13/91 | 60* | 241 |
| | 05/16/91 | 60 | 128 |
| B.R. (chondrocalcinosis) | 08/27/91 | 0 | 384 |
| | 09/11/91 | 60 | 343 |

*Through a misunderstanding the patient had been taking diltiazem for only one day (30 mg. b.i.d.) and had just taken his first 30 mg dose of the second day just prior to the blood sample.

TABLE 3

EVIDENCE SUPPORTING OUR WORKING HYPOTHESIS OBTAINED FROM THE ASSAY OF INTRACELLULAR PYROPHOSPHATE IN MONONUCLEAR CELLS OF PERIPHERAL BLOOD

| VOLUNTEERS STUDIED | DIAGNOSIS | PPi (pmols/$10^6$ Cells) | |
|---|---|---|---|
| 30 | OSTEOARTHRITIS | MEAN | 234 |
| | | S.D. | 137 |
| | | S.E.M. | 25 |
| 26 | NORMAL | MEAN | 140 |
| | | S.D. | 59.4 |
| | | S.E.M. | 11.6 |

OUR STATISTICIAN SHOWED COMPARABLE AGES AND DISTRIBUTIONS BETWEEN THE OSTEOARTHRITIS AND THE NORMAL STUDENTS T TEST SHOWED A P < .001, INDICATING DEFINITE SIGNIFICANCE BETWEEN THE TWO GROUPS. THIS DATA PROVIDES EVIDENCE FOR THE VALIDITY OF OUR HYPOTHESIS.

What is claimed is:

1. A method for reducing calcium pyrophosphate crystal deposition so as to treat an animal with pyrophosphate gout comprising administering an effective amount of a calcium antagonist to said animal, thereby reducing calcium pyrophosphate crystal deposition in the animal.

2. The method of claim 1, wherein the animal is a mammal.

3. The method of claim 2, wherein the mammal is a human.

4. The method of claim 1, wherein the calcium antagonist is diltiazem.

5. The method of claim 1, wherein the calcium antagonist is nifedipine.

6. A method for reducing calcium pyrophosphate crystal deposition in an animal in need thereof comprising administering an effective amount of a calcium antagonist to said animal, thereby reducing calcium pyrophosphate crystal deposition in the animal.

7. The method of claim 6, wherein the animal is a mammal.

8. The method of claim 7, wherein the mammal is a human.

9. The method of claim 6, wherein the calcium antagonist is diltiazem.

10. The method of claim 6, wherein the calcium antagonist is nifedipine.

* * * * *